United States Patent
Mignogna et al.

(10) Patent No.: US 9,487,599 B2
(45) Date of Patent: Nov. 8, 2016

(54) CATALYST COMPONENTS FOR THE POLYMERIZATION OF OLEFINS

(71) Applicant: Basell Poliolefine Italia S.r.l., Milan (IT)

(72) Inventors: Alessandro Mignogna, Ferrara (IT); Simona Guidotti, Ferrara (IT); Giampiero Morini, Ferrara (IT); Joachim T. M. Pater, Ferrara (IT)

(73) Assignee: Basell Poliolefine Italia S.r.l., Milan (IT)

( * ) Notice: Subject to any disclaimer, the term of this patent is extended or adjusted under 35 U.S.C. 154(b) by 0 days.

(21) Appl. No.: 14/383,838

(22) PCT Filed: Mar. 5, 2013

(86) PCT No.: PCT/EP2013/054399
§ 371 (c)(1),
(2) Date: Sep. 8, 2014

(87) PCT Pub. No.: WO2013/131912
PCT Pub. Date: Sep. 12, 2013

(65) Prior Publication Data
US 2015/0133289 A1    May 14, 2015

Related U.S. Application Data

(60) Provisional application No. 61/607,635, filed on Mar. 7, 2012.

(30) Foreign Application Priority Data

Mar. 7, 2012 (EP) .................................. 12158334

(51) Int. Cl.
*B01J 31/14* (2006.01)
*C08F 4/654* (2006.01)
*C08F 4/10* (2006.01)
*C08F 4/649* (2006.01)
*C07C 69/96* (2006.01)
*C08F 110/06* (2006.01)

(52) U.S. Cl.
CPC ............. *C08F 4/6494* (2013.01); *C07C 69/96* (2013.01); *C08F 4/6543* (2013.01); *C08F 110/06* (2013.01); *C07C 2103/18* (2013.01)

(58) Field of Classification Search
None
See application file for complete search history.

(56) References Cited

U.S. PATENT DOCUMENTS 7,388,061 B2    6/2008  Gao et al.

FOREIGN PATENT DOCUMENTS

WO    WO-2011068775 A1    6/2011

OTHER PUBLICATIONS

PCT International Sesarch Report and the Written Opinion—Mailed Nov. 10, 2013 for Corresponding PCT/EP2013/054399.

*Primary Examiner* — Yun Qian

(57) ABSTRACT

Catalyst component for the polymerization of olefins comprising Mg, Ti and an electron donor compound of the following formula (I)

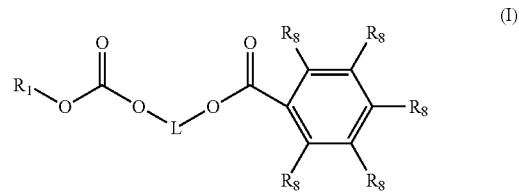

In which $R_1$ groups are selected from $C_1$-$C_{15}$ hydrocarbon groups, $R_8$ groups, equal or different to each other, are selected from hydrogen, halogen and $C_1$-$C_{15}$ hydrocarbon groups, optionally containing an heteroatom selected from halogen, O, P, S, N and Si and L is a divalent hydrocarbon group optionally containing heteroatoms selected from halogen, O, P, S, N and Si.

18 Claims, No Drawings

US 9,487,599 B2

CATALYST COMPONENTS FOR THE POLYMERIZATION OF OLEFINS

This application is the U.S. National Phase of PCT International Application PCT/EP2013/054399, filed Mar. 5, 2013, claiming benefit of priority to European Patent Application No. 12158344.8 filed Mar. 7, 2012, and benefit of priority under 35 U.S.C. §119(e) of U.S. Provisional Application No. 61/607,635 filed Mar. 7, 2012, the contents of which are incorporated herein by reference in their entirety.

FIELD OF THE INVENTION

The present disclosure relates to catalyst components for the polymerization of olefins, in particular propylene, comprising a Mg dihalide based support on which are supported Ti atoms and at least an electron donor selected from a specific class of electron donor compounds. The present disclosure further relates to the catalysts obtained from said components and to their use in processes for the polymerization of olefins in particular propylene.

BACKGROUND OF THE INVENTION

Catalyst components of the Ziegler-Natta type for the stereospecific polymerization of olefins are widely known in the art. The latest developed catalysts for propylene polymerization comprise a solid catalyst component, constituted by a magnesium dihalide on which are supported a titanium compound and an internal electron donor compound, used in combination with an Al-alkyl compound and often with an external donor which is needed in order to obtain higher isotacticity. One of the preferred classes of internal donors is constituted by the esters of phthalic acid, diisobutylphthalate being the most used. The phthalates are used as internal donors in combination with alkylalkoxysilanes as external donor. This catalyst system is capable of giving good performances in terms of activity, and propylene polymers with high isotacticity and xylene insolubility endowed with an intermediate molecular weight distribution.

Use of some phthalates however has been recently addressed as involving potential toxicity problems and therefore research activity have been devoted to find alternative classes of donor capable of replacing phthalates in terms of both performances and quality of the product.

One of the most interesting classes is that described in U.S. Pat. No. 7,388,061 disclosing esters belonging to the formula $R_1$—CO—O—$CR_3R_4$—A—$CR_5R_6$—O—CO—$R_2$ in which $R_1$ and $R_2$ groups, which may be identical or different, can be substituted or unsubstituted hydrocarbyl having 1 to 20 carbon atoms, $R_3$-$R_6$ groups, which may be identical or different, can be selected from the group consisting of hydrogen, halogen or substituted or unsubstituted hydrocarbyl having 1 to 20 carbon atoms, $R_1$-$R_6$ groups optionally contain one or more hetero-atoms replacing carbon, hydrogen atom or the both, said hetero-atom is selected from the group consisting of nitrogen, oxygen, sulfur, silicon, phosphorus and halogen atom, two or more of $R_3$-$R_6$ groups can be linked to form saturated or unsaturated monocyclic or polycyclic ring; A is a single bond or bivalent linking group with chain length between two free radicals being 1-10 atoms, wherein said bivalent linking group is selected from the group consisting of aliphatic, alicyclic and aromatic bivalent radicals, and can carry $C_1$-$C_{20}$ linear or branched substituents; one or more of carbon atoms and/or hydrogen atoms on above-mentioned bivalent linking group and substituents can be replaced by a hetero-atom selected from the group consisting of nitrogen, oxygen, sulfur, silicon, phosphorus, and halogen atom, and two or more said substituents on the linking group as well as above-mentioned $R_3$-$R_6$ groups can be linked to form saturated or unsaturated monocyclic or polycyclic ring.

The very broad formula reported encompass several structures with different performances. Within this general class the variety of performances is very high as some structures generate catalyst components showing activities and sterospecificities of interest while other structures make poor catalysts.

WO2011/068775 describes three and four atoms bridged dicarbonates compounds as internal donors in propylene polymerization. Some of the structures derive from the same diols disclosed in U.S. Pat. No. 7,388,061 with the difference that they are then formally esterified with chloroformate derivatives instead of aromatic acids (benzoic) derivatives. According to this patent the preferred structures are those in which the diol portion is part of an aromatic mono (phenyl) or polycyclic (naphthyl) group. The present applicant tests carried out on pentadiol dicarbonate derivative has shown very poor results indicating that for the same diol based structure, replacing the aromatic acid derivatives with the chloroformate derivatives carries a pronounced worsening of the properties particularly in terms of stereospecificity.

Based on this fact it has been very surprising to discover that mixed ester/carbonates of diols not only do not show worsening of the properties in respect of the analogue diesters but in some cases show an improvement of the same properties.

SUMMARY OF THE INVENTION

Accordingly, an object of the present disclosure is a catalyst component for the polymerization of olefins comprising Mg, Ti and an electron donor compound of the following formula (I)

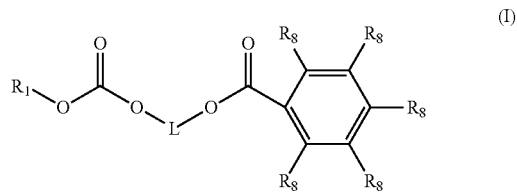

In which $R_1$ groups are selected from $C_1$-$C_{15}$ hydrocarbon groups, $R_8$ groups, equal or different to each other, are selected from hydrogen, halogen and $C_1$-$C_{15}$ hydrocarbon groups, optionally containing an heteroatom selected from halogen, O, P, S, N and Si and L is a divalent hydrocarbon group possibly containing heteroatoms selected from halogen, O, P, S, N and Si.

For all the structures described in the present application, preferred $R_1$ groups are selected from $C_1$-$C_{10}$ hydrocarbon groups, more preferably from $C_1$-$C_{10}$ alkyl groups and especially from $C_1$-$C_4$ linear alkyl groups. Ethyl is a an especially preferred $R_1$ group. Moreover, it is also of general applicability the fact the preferred embodiment in which at least one of $R_8$ is different from hydrogen and preferably selected from $C_1$-$C_{15}$ hydrocarbon groups or halogen. In a most preferred embodiment only one of $R_8$ groups is different from hydrogen. Among hydrocarbon groups preferred substitutents are $C_1$-$C_{10}$ alkyl groups, $C_6$-$C_{14}$ aryl groups, $C_3$-$C_{15}$ cycloalkyl groups, and $C_7$-$C_{15}$ arylalkyl or alkylaryl groups. More preferably, they can be $C_1$-$C_{10}$ alkyl groups and even more preferably linear $C_1$-$C_5$ alkyl groups. The hydrocarbon substituents are preferably located in 4-position.

Halogens are also preferred substituents, and among them Cl, Br and F are the preferred halogens. Cl being the most preferred. Preferred positions are meta and/or para. Also other positions in addition to meta and/or para could be substituted with halogens and/or hydrocarbon groups.

DETAILED DESCRIPTION OF THE INVENTION

In the structure of formula (I) preferably, L is a divalent hydrocarbon group having a spacing chain between the two oxygen linked to it of from 2 to 6 carbon atoms and in which, independently, the said carbon atoms can be replaced by heteroatoms selected from halogen, O, P, S, N and Si and the hydrogen atom of the said divalent hydrocarbon group can, independently, be replaced by halogen or $C_1$-$C_{15}$ hydrocarbon groups, optionally containing an heteroatom selected from halogen, P, S, N and Si, which can be linked together and/or with the carbon atoms of said divalent group to form saturated or unsaturated mono or polycyclic rings.

In particular, L is a divalent bridging group selected from $C_1$-$C_{20}$ alkylidene, $C_3$-$C_{20}$ cycloalkylidene, $C_6$-$C_{20}$ arylidene, $C_7$-$C_{20}$ alkylarylidene, or $C_7$-$C_{20}$ arylalkylidene radicals optionally containing heteroatoms selected from halogen, O, P, S, N and Si.

Particularly preferred structures are those of formula (II) below

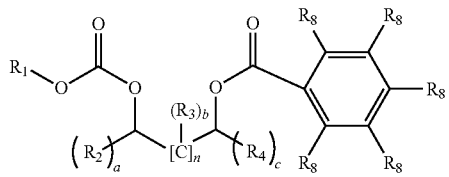

(II)

in which $R_1$ groups and $R_8$ groups have the same meaning as mentioned above, $R_2$ to $R_4$ groups, equal to or different from each other, are hydrogen or $C_1$-$C_{15}$ hydrocarbon groups, optionally containing an heteroatom selected from halogen, P, S, N and Si, two or more of said groups which can be linked together to form a saturated or unsaturated mono or polycyclic; n is an integer ranging from 0 to 3 and the indexes a, b, and c are, independently, 1 or 2.

In the structure (II) n is preferably 0 or 1. When n is 0, according to a preferred embodiment, both the indexes a and c are 1 and the groups $R_2$ and $R_4$ are fused together to form a phenyl ring which can be substituted according to formula IIa below:

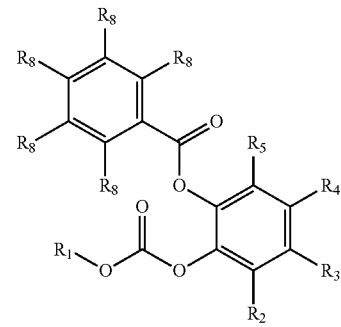

(IIa)

n which $R_1$ and $R_8$, have the same meaning described above, $R_2$-$R_5$ groups are selected from hydrogen or $C_1$-$C_{10}$ hydrocarbon groups, more preferably from hydrogen and $C_1$-$C_{10}$ alkyl groups. In a very preferred embodiment two $R_2$ to $R_5$ groups are hydrogen and the other two are selected from or C1-C10 linear or branched alkyl groups. Particularly preferred positions of the ring where substitution of hydrogen atoms takes place are positions 3 and 5. Preferred alkyl groups are methyl, ethyl, n-propyl, isopropyl, n-butyl, isobutyl, tert-butyl, 2-ethyl-hexyl. Among them methyl and tert-butyl are the most preferred.

According to another embodiment when n is 0 both the indexes a and c are 2 and the groups $R_2$ and $R_4$ are, independently, selected from hydrogen and $C_1$-$C_{10}$ alkyl groups, preferably from $C_1$-$C_5$ alkyl groups and more preferably from linear $C_1$-$C_5$ alkyl groups. In an especially preferred embodiment, both $R_2$ and $R_4$ are methyl.

When n is 1, a specific group of structures is that in which $R_1$ and $R_8$ have the same meaning specified above, b is 0 and the groups $R_2$ and $R_4$ are fused together to form a naphtyl radical possibly substituted with halogen and/or $C_1$-$C_{10}$ hydrocarbon groups optionally containing heteroatoms selected from halogen, P, S, N and Si.

In another embodiment b is 1 and the radicals $R_2$ and $R_3$ or $R_3$ and $R_4$ are fused together to form a phenyl ring possibly substituted. Preferred substitution is with $C_1$-$C_{10}$ linear or branched alkyl groups. Particularly preferred positions of the ring where substitution of hydrogen atoms take place are positions 3 and 5. Substitution in those positions with methyl and tert-butyl respectively is especially preferred.

When n is 1 and the index a, b, and c are also 1 preferred structures are those of the formula (III) below

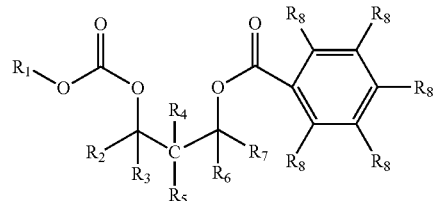

(III)

in which $R_1$ groups are selected from $C_1$-$C_{15}$ hydrocarbon groups, $R_2$ to $R_7$ groups, equal to or different from each other, are hydrogen or $C_1$-$C_{15}$ hydrocarbon groups, optionally containing an heteroatom selected from halogen, P, S, N and Si, two or more of said groups which can be linked together to form a saturated or unsaturated cycle; $R_8$ groups, equal or different to each other, are selected from hydrogen, halogen and $C_1$-$C_{15}$ hydrocarbon groups, optionally containing an heteroatom selected from halogen, P, S, N and Si.

Preferably in the structure of formula (III) $R_4$ and $R_5$ independently, are hydrogen or $C_1$-$C_5$ alkyl groups. More preferably, they are both hydrogen.

A particular interesting subgroup of structures is constituted by those of formula (IV) below

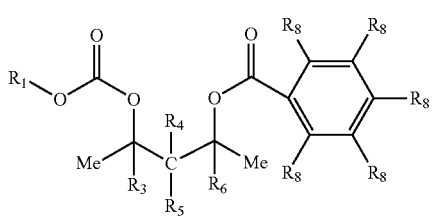

In which $R_1$ to $R_8$, have the same meaning described above.

Also in this case $R_3$-$R_6$ groups are selected from hydrogen or $C_1$-$C_{10}$ hydrocarbon groups, more preferably from hydrogen and $C_1$-$C_{10}$ alkyl groups. In a very preferred embodiment $R_3$ to $R_6$ are hydrogen.

It has been found that the new donors described in the catalyst of the present disclosure may exist in spatial configurations that are more preferred than others with respect to (a) capability of being fixed in the catalyst component and (b) catalyst performances.

With particular reference to the donors of formulae (III) and (IV) it has been observed that the compounds in which the oxygen of the diol chain are syn configuration show higher affinity for the catalyst and improved performances. The syn configuration is therefore the preferred one. Preferred catalyst components contain more than 50%, preferably more than 70 and more preferably more than 90% of the total amount of donor with a syn configuration.

Non limiting examples of structures according formulae I to IV are the following:

4-(((4-chlorophenoxy)carbonyl)oxy)pentan-2-yl 4-butylbenzoate,
4-(((4-chlorophenoxy)carbonyl)oxy)pentan-2-yl 4-chlorobenzoate,
4-(((4-chlorophenoxy)carbonyl)oxy)pentan-2-yl 4-ethylbenzoate,
4-(((4-chlorophenoxy)carbonyl)oxy)pentan-2-yl 4-methylbenzoate,
4-(((4-chlorophenoxy)carbonyl)oxy)pentan-2-yl 4-propylbenzoate,
4-(((neopentyloxy)carbonyl)oxy)pentan-2-yl 4-butylbenzoate,
4-(((neopentyloxy)carbonyl)oxy)pentan-2-yl 4-chlorobenzoate,
4-(((neopentyloxy)carbonyl)oxy)pentan-2-yl 4-ethylbenzoate,
4-(((neopentyloxy)carbonyl)oxy)pentan-2-yl 4-methylbenzoate,
4-(((neopentyloxy)carbonyl)oxy)pentan-2-yl 4-propylbenzoate,
4-((butoxycarbonyl)oxy)pentan-2-yl 4-butylbenzoate,
4-((butoxycarbonyl)oxy)pentan-2-yl 4-chlorobenzoate,
4-((butoxycarbonyl)oxy)pentan-2-yl 4-ethylbenzoate,
4-((butoxycarbonyl)oxy)pentan-2-yl 4-methylbenzoate,
4-((butoxycarbonyl)oxy)pentan-2-yl 4-propylbenzoate,
4-((ethoxycarbonyl)oxy)pentan-2-yl 4-butylbenzoate,
4-((ethoxycarbonyl)oxy)pentan-2-yl 4-chlorobenzoate,
4-((ethoxycarbonyl)oxy)pentan-2-yl 4-ethylbenzoate,
4-((ethoxycarbonyl)oxy)pentan-2-yl 4-methylbenzoate,
4-((ethoxycarbonyl)oxy)pentan-2-yl 4-propylbenzoate,
4-((isobutoxycarbonyl)oxy)pentan-2-yl 4-butylbenzoate,
4-((isobutoxycarbonyl)oxy)pentan-2-yl 4-chlorobenzoate,
4-((isobutoxycarbonyl)oxy)pentan-2-yl 4-ethylbenzoate,
4-((isobutoxycarbonyl)oxy)pentan-2-yl 4-methylbenzoate,
4-((isobutoxycarbonyl)oxy)pentan-2-yl 4-propylbenzoate,
4-((methoxycarbonyl)oxy)pentan-2-yl 4-butylbenzoate,
4-((methoxycarbonyl)oxy)pentan-2-yl 4-chlorobenzoate,
4-((methoxycarbonyl)oxy)pentan-2-yl 4-ethylbenzoate,
4-((methoxycarbonyl)oxy)pentan-2-yl 4-methylbenzoate,
4-((methoxycarbonyl)oxy)pentan-2-yl 4-propylbenzoate,
4-((phenoxycarbonyl)oxy)pentan-2-yl 4-butylbenzoate,
4-((phenoxycarbonyl)oxy)pentan-2-yl 4-chlorobenzoate,
4-((phenoxycarbonyl)oxy)pentan-2-yl 4-ethylbenzoate,
4-((phenoxycarbonyl)oxy)pentan-2-yl 4-methylbenzoate,
4-((phenoxycarbonyl)oxy)pentan-2-yl 4-propylbenzoate,
4-(((4-chlorophenoxy)carbonyl)oxy)pentan-2-yl 3-chlorobenzoate,
4-(((neopentyloxy)carbonyl)oxy)pentan-2-yl 3-chlorobenzoate,
4-((butoxycarbonyl)oxy)pentan-2-yl 3-chlorobenzoate,
4-((ethoxycarbonyl)oxy)pentan-2-yl 3-chlorobenzoate,
4-((isobutoxycarbonyl)oxy)pentan-2-yl 3-chlorobenzoate,
4-((methoxycarbonyl)oxy)pentan-2-yl 3-chlorobenzoate,
4-((phenoxycarbonyl)oxy)pentan-2-yl 3-chlorobenzoate,
3-(1-((ethoxycarbonyl)oxy)ethyl)-5-methylhexan-2-yl 4-butylbenzoate,
3-(1-((ethoxycarbonyl)oxy)ethyl)-5-methylhexan-2-yl 4-chlorobenzoate,
3-(1-((ethoxycarbonyl)oxy)ethyl)-5-methylhexan-2-yl 4-propylbenzoate,
3-benzyl-4-((ethoxycarbonyl)oxy)pentan-2-yl 4-butylbenzoate,
3-benzyl-4-((ethoxycarbonyl)oxy)pentan-2-yl 4-chlorobenzoate,
3-benzyl-4-((ethoxycarbonyl)oxy)pentan-2-yl 4-propylbenzoate,
4-((ethoxycarbonyl)oxy)-3-isopropylpentan-2-yl 4-butylbenzoate,
4-((ethoxycarbonyl)oxy)-3-isopropylpentan-2-yl 4-chlorobenzoate,
4-((ethoxycarbonyl)oxy)-3-isopropylpentan-2-yl 4-propylbenzoate,
4-((ethoxycarbonyl)oxy)-3-methylpentan-2-yl 4-butylbenzoate,
4-((ethoxycarbonyl)oxy)-3-methylpentan-2-yl 4-chlorobenzoate,
4-((ethoxycarbonyl)oxy)-3-methylpentan-2-yl 4-propylbenzoate,
4-ethyl-5-((phenoxycarbonyl)oxy)heptan-3-yl 4-butylbenzoate,
4-ethyl-5-((phenoxycarbonyl)oxy)heptan-3-yl 4-chlorobenzoate,
4-ethyl-5-((phenoxycarbonyl)oxy)heptan-3-yl 4-propylbenzoate,
5-((butoxycarbonyl)oxy)-4-ethylheptan-3-yl 4-butylbenzoate,
5-((butoxycarbonyl)oxy)-4-ethylheptan-3-yl 4-chlorobenzoate,
5-((butoxycarbonyl)oxy)-4-ethylheptan-3-yl 4-propylbenzoate,
5-((ethoxycarbonyl)oxy)-4-ethylheptan-3-yl 4-butylbenzoate, 5-((ethoxycarbonyl)oxy)-4-ethylheptan-3-yl 4-chlorobenzoate,
5-((ethoxycarbonyl)oxy)-4-ethylheptan-3-yl 4-propylbenzoate,
(9-(((butoxycarbonyl)oxy)methyl)-9H-fluoren-9-yl)methyl 4-butylbenzoate,
(9-(((butoxycarbonyl)oxy)methyl)-9H-fluoren-9-yl)methyl 4-chlorobenzoate,
(9-(((butoxycarbonyl)oxy)methyl)-9H-fluoren-9-yl)methyl 4-propylbenzoate,
(9-(((ethoxycarbonyl)oxy)methyl)-9H-fluoren-9-yl)methyl 4-butylbenzoate,
(9-(((ethoxycarbonyl)oxy)methyl)-9H-fluoren-9-yl)methyl 4-chlorobenzoate,
(9-(((ethoxycarbonyl)oxy)methyl)-9H-fluoren-9-yl)methyl 4-propylbenzoate,
(9-(((phenoxycarbonyl)oxy)methyl)-9H-fluoren-9-yl)methyl 4-butylbenzoate
(9-(((phenoxycarbonyl)oxy)methyl)-9H-fluoren-9-yl)methyl 4-chlorobenzoate,
(9-(((phenoxycarbonyl)oxy)methyl)-9H-fluoren-9-yl)methyl 4-propylbenzoate,
2-(((butoxycarbonyl)oxy)methyl)-2-isobutyl-4-methylpentyl 4-butylbenzoate,
2-(((butoxycarbonyl)oxy)methyl)-2-isobutyl-4-methylpentyl 4-chlorobenzoate,
2-(((butoxycarbonyl)oxy)methyl)-2-isobutyl-4-methylpentyl 4-propylbenzoate,
2-(((ethoxycarbonyl)oxy)methyl)-2-isobutyl-4-methylpentyl 4-butylbenzoate,
2-(((ethoxycarbonyl)oxy)methyl)-2-isobutyl-4-methylpentyl 4-chlorobenzoate,
2-(((ethoxycarbonyl)oxy)methyl)-2-isobutyl-4-methylpentyl 4-propylbenzoate,
2-isobutyl-4-methyl-2-(((phenoxycarbonyl)oxy)methyl)pentyl 4-butylbenzoate,
2-isobutyl-4-methyl-2-(((phenoxycarbonyl)oxy)methyl)pentyl 4-chlorobenzoate,
2-isobutyl-4-methyl-2-(((phenoxycarbonyl)oxy)methyl)pentyl 4-propylbenzoate,
2,2-dimethyl-3-((phenoxycarbonyl)oxy)propyl 4-butylbenzoate,
2,2-dimethyl-3-((phenoxycarbonyl)oxy)propyl 4-chlorobenzoate,
2,2-dimethyl-3-((phenoxycarbonyl)oxy)propyl 4-propylbenzoate,
3-((butoxycarbonyl)oxy)-2,2-dimethylpropyl 4-butylbenzoate,
3-((butoxycarbonyl)oxy)-2,2-dimethylpropyl 4-chlorobenzoate,
3-((butoxycarbonyl)oxy)-2,2-dimethylpropyl 4-propylbenzoate,
3-((ethoxycarbonyl)oxy)-2,2-dimethylpropyl 4-butylbenzoate,
3-((ethoxycarbonyl)oxy)-2,2-dimethylpropyl 4-chlorobenzoate,
3-((ethoxycarbonyl)oxy)-2,2-dimethylpropyl 4-propylbenzoate,
2-(((butoxycarbonyl)oxy)methyl)-2-isopropyl-5-methylhexyl 4-butylbenzoate,
2-(((butoxycarbonyl)oxy)methyl)-2-isopropyl-5-methylhexyl 4-chlorobenzoate,
2-(((butoxycarbonyl)oxy)methyl)-2-isopropyl-5-methylhexyl 4-propylbenzoate,
2-(((ethoxycarbonyl)oxy)methyl)-2-isopropyl-5-methylhexyl 4-butylbenzoate,
2-(((ethoxycarbonyl)oxy)methyl)-2-isopropyl-5-methylhexyl 4-chlorobenzoate,
2-(((ethoxycarbonyl)oxy)methyl)-2-isopropyl-5-methylhexyl 4-propylbenzoate,
2-isopropyl-5-methyl-2-(((phenoxycarbonyl)oxy)methyl)hexyl 4-butylbenzoate,
2-isopropyl-5-methyl-2-(((phenoxycarbonyl)oxy)methyl)hexyl 4-chlorobenzoate,
2-isopropyl-5-methyl-2-(((phenoxycarbonyl)oxy)methyl)hexyl 4-propylbenzoate,
8-((butoxycarbonyl)oxy)naphthalen-1-yl 4-butylbenzoate,
8-((butoxycarbonyl)oxy)naphthalen-1-yl 4-chlorobenzoate,
8-((butoxycarbonyl)oxy)naphthalen-1-yl 4-propylbenzoate,
8-((ethoxycarbonyl)oxy)naphthalen-1-yl 4-butylbenzoate,
8-((ethoxycarbonyl)oxy)naphthalen-1-yl 4-chlorobenzoate,
8-((ethoxycarbonyl)oxy)naphthalen-1-yl 4-propylbenzoate,
8-((phenoxycarbonyl)oxy)naphthalen-1-yl 4-butylbenzoate,
8-((phenoxycarbonyl)oxy)naphthalen-1-yl 4-chlorobenzoate,
8-((phenoxycarbonyl)oxy)naphthalen-1-yl 4-propylbenzoate,
2-((butoxycarbonyl)oxy)-5-(tert-butyl)-3-methylphenyl 4-butylbenzoate,
2-((butoxycarbonyl)oxy)-5-(tert-butyl)-3-methylphenyl 4-chlorobenzoate,
2-((butoxycarbonyl)oxy)-5-(tert-butyl)-3-methylphenyl 4-propylbenzoate,
5-(tert-butyl)-2-((ethoxycarbonyl)oxy)-3-methylphenyl 4-butylbenzoate,
5-(tert-butyl)-2-((ethoxycarbonyl)oxy)-3-methylphenyl 4-chlorobenzoate,
5-(tert-butyl)-2-((ethoxycarbonyl)oxy)-3-methylphenyl 4-propylbenzoate,
5-(tert-butyl)-3-methyl-2-((phenoxycarbonyl)oxy)phenyl 4-butylbenzoate,
5-(tert-butyl)-3-methyl-2-((phenoxycarbonyl)oxy)phenyl 4-chlorobenzoate,
5-(tert-butyl)-3-methyl-2-((phenoxycarbonyl)oxy)phenyl 4-propylbenzoate,
2-((butoxycarbonyl)oxy)-4-(tert-butyl)-6-methylphenyl 4-butylbenzoate,
2-((butoxycarbonyl)oxy)-4-(tert-butyl)-6-methylphenyl 4-chlorobenzoate,
2-((butoxycarbonyl)oxy)-4-(tert-butyl)-6-methylphenyl 4-propylbenzoate,
4-(tert-butyl)-2-((ethoxycarbonyl)oxy)-6-methylphenyl 4-butylbenzoate,
4-(tert-butyl)-2-((ethoxycarbonyl)oxy)-6-methylphenyl 4-chlorobenzoate,
4-(tert-butyl)-2-((ethoxycarbonyl)oxy)-6-methylphenyl 4-propylbenzoate,
4-(tert-butyl)-2-methyl-6-((phenoxycarbonyl)oxy)phenyl 4-butylbenzoate,
4-(tert-butyl)-2-methyl-6-((phenoxycarbonyl)oxy)phenyl 4-chlorobenzoate,
4-(tert-butyl)-2-methyl-6-((phenoxycarbonyl)oxy)phenyl 4-propylbenzoate,
2,4-diisopropyl-6-((phenoxycarbonyl)oxy)phenyl 4-butylbenzoate,
2,4-diisopropyl-6-((phenoxycarbonyl)oxy)phenyl 4-chlorobenzoate,
2,4-diisopropyl-6-((phenoxycarbonyl)oxy)phenyl 4-propylbenzoate,
2-((butoxycarbonyl)oxy)-4,6-diisopropylphenyl 4-butylbenzoate,
2-((butoxycarbonyl)oxy)-4,6-diisopropylphenyl 4-chlorobenzoate, 2-((butoxycarbonyl)oxy)-4,6-diisopropylphenyl 4-propylbenzoate,
2-((ethoxycarbonyl)oxy)-4,6-diisopropylphenyl 4-butylbenzoate,
2-((ethoxycarbonyl)oxy)-4,6-diisopropylphenyl 4-chlorobenzoate,
2-((ethoxycarbonyl)oxy)-4,6-diisopropylphenyl 4-propylbenzoate,
2-((butoxycarbonyl)oxy)-3,5-diisopropylphenyl 4-butylbenzoate,
2-((butoxycarbonyl)oxy)-3,5-diisopropylphenyl 4-chlorobenzoate,
2-((butoxycarbonyl)oxy)-3,5-diisopropylphenyl 4-propylbenzoate,
2-((ethoxycarbonyl)oxy)-3,5-diisopropylphenyl 4-butylbenzoate,
2-((ethoxycarbonyl)oxy)-3,5-diisopropylphenyl 4-chlorobenzoate,
2-((ethoxycarbonyl)oxy)-3,5-diisopropylphenyl 4-propylbenzoate,
3,5-diisopropyl-2-((phenoxycarbonyl)oxy)phenyl 4-butylbenzoate,
3,5-diisopropyl-2-((phenoxycarbonyl)oxy)phenyl 4-chlorobenzoate,
3,5-diisopropyl-2-((phenoxycarbonyl)oxy)phenyl 4-propylbenzoate,
3-((ethoxycarbonyl)oxy)-2-methylbutyl 4-butylbenzoate,
3-((ethoxycarbonyl)oxy)-2-methylbutyl 4-chlorobenzoate,
3-((ethoxycarbonyl)oxy)-2-methylbutyl 4-propylbenzoate,
3-((ethoxycarbonyl)oxy)-2-methylbutyl benzoate,
3-((ethoxycarbonyl)oxy)-2-methylpentyl 4-butylbenzoate,
3-((ethoxycarbonyl)oxy)-2-methylpentyl 4-chlorobenzoate,
3-((ethoxycarbonyl)oxy)-2-methylpentyl 4-propylbenzoate,
3-((ethoxycarbonyl)oxy)-2-methylpentyl benzoate,
3-((ethoxycarbonyl)oxy)butyl 4-butylbenzoate,
3-((ethoxycarbonyl)oxy)butyl 4-chlorobenzoate,
3-((ethoxycarbonyl)oxy)butyl 4-propylbenzoate,
3-((ethoxycarbonyl)oxy)butyl benzoate,
3-((ethoxycarbonyl)oxy)pentyl 4-butylbenzoate,
3-((ethoxycarbonyl)oxy)pentyl 4-chlorobenzoate,
3-((ethoxycarbonyl)oxy)pentyl 4-propylbenzoate,
3-((ethoxycarbonyl)oxy)pentyl benzoate,
1-((ethoxycarbonyl)oxy)-2-methylpentan-3-yl 4-butylbenzoate,
1-((ethoxycarbonyl)oxy)-2-methylpentan-3-yl 4-chlorobenzoate,
1-((ethoxycarbonyl)oxy)-2-methylpentan-3-yl 4-propylbenzoate,
1-((ethoxycarbonyl)oxy)-2-methylpentan-3-yl benzoate,
1-((ethoxycarbonyl)oxy)pentan-3-yl 4-butylbenzoate,
1-((ethoxycarbonyl)oxy)pentan-3-yl 4-chlorobenzoate,
1-((ethoxycarbonyl)oxy)pentan-3-yl 4-propylbenzoate,
1-((ethoxycarbonyl)oxy)pentan-3-yl benzoate,
4-((ethoxycarbonyl)oxy)-3-methylbutan-2-yl 4-butylbenzoate,
4-((ethoxycarbonyl)oxy)-3-methylbutan-2-yl 4-chlorobenzoate,
4-((ethoxycarbonyl)oxy)-3-methylbutan-2-yl 4-propylbenzoate,
4-((ethoxycarbonyl)oxy)-3-methylbutan-2-yl benzoate,
4-((ethoxycarbonyl)oxy)butan-2-yl 4-butylbenzoate,
4-((ethoxycarbonyl)oxy)butan-2-yl 4-chlorobenzoate,
4-((ethoxycarbonyl)oxy)butan-2-yl 4-propylbenzoate,
4-((ethoxycarbonyl)oxy)butan-2-yl benzoate,
4-((ethoxycarbonyl)oxy)pentan-2-yl benzoate,
4-((ethoxycarbonyl)oxy)-3-methylpentan-2-yl benzoate,
3-benzyl-4-((ethoxycarbonyl)oxy)pentan-2-yl benzoate,
5-((ethoxycarbonyl)oxy)-4-ethylheptan-3-yl benzoate,
(9-((((ethoxycarbonyl)oxy)methyl)-9H-fluoren-9-yl)methyl benzoate,
2-(((ethoxycarbonyl)oxy)methyl)-2-isobutyl-4-methylpentyl benzoate,
2-(((ethoxycarbonyl)oxy)methyl)-2-isopropyl-5-methylhexyl benzoate,
3-((ethoxycarbonyl)oxy)-2,2-dimethylpropyl benzoate,
8-((ethoxycarbonyl)oxy)naphthalen-1-yl benzoate,
5-(tert-butyl)-2-((ethoxycarbonyl)oxy)-3-methylphenyl benzoate,
4-(tert-butyl)-2-((ethoxycarbonyl)oxy)-6-methylphenyl benzoate,
2-((ethoxycarbonyl)oxy)-4,6-diisopropylphenyl benzoate,
2-((ethoxycarbonyl)oxy)-3,5-diisopropylphenyl benzoate.

As explained above, the catalyst components of the disclosure comprise, in addition to the above electron donors, Ti, Mg and halogen. In particular, the catalyst components comprise a titanium compound, having at least a Ti-halogen bond and the above mentioned electron donor compounds supported on a Mg halide. The magnesium halide is preferably $MgCl_2$ in active form which is widely known from the patent literature as a support for Ziegler-Natta catalysts. Patents U.S. Pat. No. 4,298,718 and U.S. Pat. No. 4,495,338 were the first to describe the use of these compounds in Ziegler-Natta catalysis. It is known from these patents that the magnesium dihalides in active form used as support or co-support in components of catalysts for the polymerization of olefins are characterized by X-ray spectra in which the most intense diffraction line that appears in the spectrum of the non-active halide is diminished in intensity and is replaced by a halo whose maximum intensity is displaced towards lower angles relative to that of the more intense line.

The preferred titanium compounds used in the catalyst component of the present disclosure are $TiCl_4$ and $TiCl_3$; furthermore, also Ti-haloalcoholates of formula $Ti(OR)_{q-y}X_y$ can be used, where q is the valence of titanium, y is a number between 1 and q–1, X is halogen and R is a hydrocarbon radical having from 1 to 10 carbon atoms.

The preparation of the solid catalyst component can be carried out according to several methods.

According to one of these methods, the magnesium dichloride in an anhydrous state, the titanium compound and the electron donor compounds are milled together under conditions in which activation of the magnesium dichloride occurs. The so obtained product can be treated one or more times with an excess of $TiCl_4$ at a temperature between 80 and 135° C. This treatment is followed by washings with hydrocarbon solvents until chloride ions disappeared. According to a further method, the product obtained by co-milling the magnesium chloride in an anhydrous state, the titanium compound and the electron donor compounds are treated with halogenated hydrocarbons such as 1,2-dichloroethane, chlorobenzene, dichloromethane etc. The treatment is carried out for a time between 1 and 4 hours and at temperature of from 40° C. to the boiling point of the halogenated hydrocarbon. Another method comprises the reaction between magnesium alcoholates or chloroalcoholates (in particular chloroalcoholates prepared according to U.S. Pat. No. 4,220,554) and an excess of $TiCl_4$ in the presence of the electron donor compounds at a temperature of about 80 to 120° C.

According to a preferred method, the solid catalyst component can be prepared by reacting a titanium compound of formula $Ti(OR)_{q-y}X_y$, where q is the valence of titanium and y is a number between 1 and q, preferably $TiCl_4$, with a magnesium chloride deriving from an adduct of formula MgCl$_2$.pROH, where p is a number between 0.1 and 6, preferably from 2 to 3.5, and R is a hydrocarbon radical having 1-18 carbon atoms. The adduct can be suitably prepared in spherical form by mixing alcohol and magnesium chloride in the presence of an inert hydrocarbon immiscible with the adduct, operating under stirring conditions at the melting temperature of the adduct (100-130° C.). Then, the emulsion is quickly quenched, thereby causing the solidification of the adduct in form of spherical particles. Examples of spherical adducts prepared according to this procedure are described in U.S. Pat. No. 4,399,054 and U.S. Pat. No. 4,469,648. The so obtained adduct can be directly reacted with Ti compound or it can be previously subjected to thermal controlled dealcoholation (80-130° C.) so as to obtain an adduct in which the number of moles of alcohol is generally lower than 3, preferably between 0.1 and 2.5. The reaction with the Ti compound can be carried out by suspending the adduct (dealcoholated or as such) in cold TiCl$_4$ (generally 0° C.); the mixture is heated up to 80-130° C. and kept at this temperature for 0.5-2 hours. The treatment with TiCl$_4$ can be carried out one or more times. The electron donor compounds can be added in the desired ratios during the treatment with TiCl$_4$. The preparation of catalyst components in spherical form are described for example in European Patent Applications EP-A-395083, EP-A-553805, EP-A-553806, EPA601525 and WO98/44001.

The solid catalyst components obtained according to the above method show a surface area (by B.E.T. method) generally between 20 and 500 m$^2$/g and preferably between 50 and 400 m$^2$/g, and a total porosity (by B.E.T. method) higher than 0.2 cm$^3$/g preferably between 0.2 and 0.6 cm$^3$/g. The porosity (Hg method) due to pores with radius up to 10.000 Å generally ranges from 0.3 to 1.5 cm$^3$/g, preferably from 0.45 to 1 cm$^3$/g.

The solid catalyst component has an average particle size ranging from 5 to 120 μm and more preferably from 10 to 100 μm.

As mentioned, in any of these preparation methods the desired electron donor compounds can be added as such or, in an alternative way, can be obtained in situ by using an appropriate precursor capable of being transformed in the desired electron donor compound by means, for example, of known chemical reactions such as etherification, alkylation, esterification, transesterification etc.

Regardless of the preparation method used, the final amount of the electron donor compound of formula (I) is such that its molar ratio with respect to the TiCl$_4$ is from 0.01 to 1, preferably from 0.05 to 0.5.

The solid catalyst components according to the present disclosure are converted into catalysts for the polymerization of olefins by reacting them with organoaluminum compounds according to known methods.

In particular, an object of the present disclosure is a catalyst for the polymerization of olefins CH$_2$=CHR, in which R is hydrogen or a hydrocarbyl radical with 1-12 carbon atoms, comprising the product obtained by contacting:
(i) the solid catalyst component as disclosed above and
(ii) an alkylaluminum compound.

The alkyl-Al compound (II) is preferably chosen among the trialkyl aluminum compounds such as for example triethylaluminum, triisobutylaluminum, tri-n-butylaluminum, tri-n-hexylaluminum, tri-n-octylaluminum. It is also possible to use alkylaluminum halides, alkylaluminum hydrides or alkylaluminum sesquichlorides, such as AlEt$_2$Cl and Al$_2$Et$_3$Cl$_3$, possibly in mixture with the above cited trialkylaluminums.

Suitable external electron-donor compounds include silicon compounds, ethers, esters, amines, heterocyclic compounds and particularly 2,2,6,6-tetramethylpiperidine and ketones. Another class of preferred external donor compounds is that of silicon compounds of formula (R$_6$)$_a$(R$_7$)$_b$Si(OR$_8$)$_c$, where a and b are integers from 0 to 2, c is an integer from 1 to 4 and the sum (a+b+c) is 4; R$_6$, R$_7$, and R$_8$, are alkyl, cycloalkyl or aryl radicals with 1-18 carbon atoms optionally containing heteroatoms. Particularly preferred are the silicon compounds in which a is 1, b is 1, c is 2, at least one of R$_6$ and R$_7$ is selected from branched alkyl, cycloalkyl or aryl groups with 3-10 carbon atoms optionally containing heteroatoms and R$_8$ is a C$_1$-C$_{10}$ alkyl group, in particular methyl. Examples of such preferred silicon compounds are methylcyclohexyldimethoxysilane (C donor), diphenyldimethoxysilane, methyl-t-butyldimethoxysilane, dicyclopentyldimethoxysilane (D donor), (2-ethylpiperidinyl)t-butyldimethoxysilane, (2-ethylpiperidinyl)thexyldimethoxysilane, (3,3,3-trifluoro-n-propyl)(2-ethylpiperidinyl)dimethoxysilane, methyl(3,3,3-trifluoro-n-propyl)dimethoxysilane. Moreover, the silicon compounds in which a is 0, c is 3, R$_7$ is a branched alkyl or cycloalkyl group, optionally containing heteroatoms, and R$_8$ is methyl are also preferred. Examples of such preferred silicon compounds are cyclohexyltrimethoxysilane, t-butyltrimethoxysilane and thexyltrimethoxysilane.

The electron donor compound (iii) is used in such an amount to give a molar ratio between the organoaluminum compound and said electron donor compound (iii) of from 0.1 to 500, preferably from 1 to 300 and more preferably from 3 to 100.

Therefore, it constitutes a further object of the present disclosure a process for the (co)polymerization of olefins CH$_2$=CHR, in which R is hydrogen or a hydrocarbyl radical with 1-12 carbon atoms, carried out in the presence of a catalyst comprising the product of the reaction between:
(i) the solid catalyst component of the disclosure;
(ii) an alkylaluminum compound and,
(iii) optionally an electron-donor compound (external donor).

The polymerization process can be carried out according to known techniques for example slurry polymerization using as diluent an inert hydrocarbon solvent, or bulk polymerization using the liquid monomer (for example propylene) as a reaction medium. Moreover, it is possible to carry out the polymerization process in gas-phase operating in one or more fluidized or mechanically agitated bed reactors.

The polymerization is generally carried out at temperature of from 20 to 120° C., preferably of from 40 to 80° C. When the polymerization is carried out in gas-phase the operating pressure is generally between 0.5 and 5 MPa, preferably between 1 and 4 MPa. In the bulk polymerization the operating pressure is generally between 1 and 8 MPa, preferably between 1.5 and 5 MPa.

The following examples are given in order to better illustrate the invention without limiting it.

EXAMPLES

Characterizations

Determination of Ti

The determination of Ti content in the solid catalyst component has been carried out via inductively coupled plasma emission spectroscopy on "I.C.P Spectrometer ARL Accuris". The sample was prepared by analytically weighting, in a "fluxy" platinum crucible", 0.1÷0.3 grams of catalyst and 3 grams of lithium metaborate/tetraborate 1/1 mixture. The crucible is placed on a weak Bunsen flame for the burning step and then after addition of some drops of KI solution inserted in a special apparatus "Claisse Fluxy" for the complete burning. The residue is collected with a 5% v/v $HNO_3$ solution and then the titanium was analyzed via ICP at a wavelength of 368.52 nm.

Determination of Internal Donor Content

The determination of the content of internal donor in the solid catalytic compound was done through gas chromatography. The solid component was dissolved in water. The solution was extracted with ethyl acetate, an internal standard was added, and a sample of the organic phase was analyzed in a gas chromatograph, to determine the amount of donor present at the starting catalyst compound.

Determination of X.I.

2.5 g of polymer and 250 ml of o-xylene were placed in a round-bottomed flask provided with a cooler and a reflux condenser and kept under nitrogen. The obtained mixture was heated to 135° C. and was kept under stirring for about 60 minutes. The final solution was allowed to cool to 25° C. under continuous stirring, and the insoluble polymer was then filtered. The filtrate was then evaporated in a nitrogen flow at 140° C. to reach a constant weight. The content of said xylene-soluble fraction is expressed as a percentage of the original 2.5 grams and then, by difference, the X.I. %.

Melt Flow Rate (MFR)

The melt flow rate MIL of the polymer was determined according to ISO 1133 (230° C., 2.16 Kg)

EXAMPLES

Procedure for Preparation of the Spherical Adduct

An initial amount of microspheroidal $MgCl_2.2.8C_2H_5OH$ was prepared according to the method described in Example 2 of WO98/44009, but operating on larger scale. The support adduct had a P50 of about 25 micron, and an ethanol content of about 56% wt.

General Procedure for the Preparation of the Solid Catalyst Component

Into a 500 ml round bottom flask, equipped with mechanical stirrer, cooler and thermometer 250 ml of $TiCl_4$ were introduced at room temperature under nitrogen atmosphere. After cooling to 0° C., while stirring, the internal donor and 10.0 g of the spherical adduct (prepared as described above) were sequentially added into the flask. The amount of charged internal donor was such to charge a Mg/donor molar ratio of 6. The temperature was raised to 100° C. and maintained for 2 hours. Thereafter, stirring was stopped, the solid product was allowed to settle and the supernatant liquid was siphoned off at 100° C. After the supernatant was removed, additional fresh $TiCl_4$ was added to reach the initial liquid volume again. The mixture was then heated at 120° C. and kept at this temperature for 1 hour. Stirring was stopped again, the solid was allowed to settle and the supernatant liquid was siphoned off.

The solid was washed with anhydrous hexane six times (6×100 ml) in temperature gradient down to 60° C. and one time (100 ml) at room temperature. The obtained solid was then dried under vacuum and analyzed.

General Procedure for the Polymerization of Propylene

A 4-liter steel autoclave equipped with a stirrer, pressure gauge, thermometer, catalyst feeding system, monomer feeding lines and thermostating jacket, was purged with nitrogen flow at 70° C. for one hour. Then, at 30° C. under propylene flow, were charged in sequence with 75 ml of anhydrous hexane, 0.76 g of $AlEt_3$, 0.076 g of dicyclopentyldimethoxysilane (D donor) and 0.006÷0.010 g of solid catalyst component. The autoclave was closed; subsequently 2.0 Nl of hydrogen were added. Then, under stirring, 1.2 kg of liquid propylene was fed. The temperature was raised to 70° C. in five minutes and the polymerization was carried out at this temperature for two hours. At the end of the polymerization, the non-reacted propylene was removed; the polymer was recovered and dried at 70° C. under vacuum for three hours. Then the polymer was weighed and fractionated with o-xylene to determine the amount of the xylene insoluble (X.I.) fraction.

EXAMPLES 1-5, AND COMPARATIVE EXAMPLES C1 AND C2

The synthesis of the donors were used in the preparation of the solid catalyst components is herebelow reported Example 1

Preparation of 4-((ethoxycarbonyl)oxy)pentan-2-yl 4-propylbenzoate

First Step:

7.9 g of 2,4-pentanediol (75.8 mmol) and 2.9 mL of ethyl chloroformate (30 mmol) are charged in a round bottom flask with 100 mL of $CH_2Cl_2$ under nitrogen. The solution is cooled to −10° C. then 2.4 mL of pyridine (30 mmol) are added dropwise slowly. Then the mixture is brought to room temperature and quenched with aqueous HCl. The organic layer is washed with water until neutral pH, then is anhydrified over $Na_2SO_4$ and the solvent is distilled off to afford 4.1 g of ethyl (4-hydroxypentan-2-yl) carbonate which is used in the second step without further purification.

Second Step:

3.6 g of ethyl (4-hydroxypentan-2-yl) carbonate (20.4 mmol) are charged in a round bottom flask, under nitrogen, with 4 g of 4-n-propylbenzoyl chloride (21.9 mmol), 1.8 mL of pyridine (22.8 mmol) and 40 mL of $CH_2Cl_2$. The mixture is heated up to 40° C. until GC shows that the reaction is completed then quenched with acidic water. The organic layer is washed with water until neutral pH, then is anhydrified over $Na_2SO_4$ and the solvent is distilled off to afford 5.3 g of 4-((ethoxycarbonyl)oxy)pentan-2-yl 4-propylbenzoate.

Example 2

Preparation of 4-((ethoxycarbonyl)oxy)pentan-2-yl 3-chlorobenzoate

The procedure is the same of Synthetic Example 1 except that 3-chlorobenzoyl chloride is used instead of 4-n-propylbenzoyl chloride.

Example 3

Preparation of 4-((ethoxycarbonyl)oxy)butan-2-yl benzoate

First Step:

4-hydroxy-2-butanone (15 g, 0.17 mol), pyridine (25 mL), and $CH_2Cl_2$ (100 mL) were cooled to 0° C. Then ethyl chloroformate (16.2 mL, 0.17 mol) was added dropwise over 50 min with stirring. After 4 h the reaction was quenched with water and diluted by CH$_2$Cl$_2$ (100 mL). The organic layer was washed sequentially with aqueous HCl, water, dried over MgSO$_4$, evaporated and distilled under vacuum to afford 17.7 g ethyl 3-oxobutyl carbonate.

Second Step:

ethyl 3-oxobutyl carbonate (16.7 g, 0.104 mol) and EtOH (150 mL) were cooled to 0° C. NaBH$_4$ (1.1 g, 0.029 mol) was added portionwise over 50 min with stirring. After 4 h the reaction was poured into solution of aqueous HCl (25 mL) in water (500 mL). The mixture was extracted by CH$_2$Cl$_2$. The organic layer was washed with water, dried over MgSO$_4$, evaporated to afford 11.8 g of ethyl 3-hydroxybutyl carbonate which was used in the next step without further purification.

Third Step:

ethyl 3-hydroxybutyl carbonate (0.1 mol), pyridine (25 mL), and CH$_2$Cl$_2$ (170 mL) was cooled to −20° C. Benzoyl chloride (0.095 mol) was added dropwise over 25 min with stirring. After 4 h the reaction was quenched with 5% aqueous HCl and was diluted by CH$_2$Cl$_2$ (150 mL). The organic layer was washed sequentially with 5% aqueous HCl, water, 5% aqueous NaOH, water, saturated solution of NH$_4$Cl, dried over MgSO$_4$, evaporated and distilled under vacuum to afford 8.9 g of 3-[(ethoxycarbonyl)oxy]-1-methylpropyl benzoate.

Example 4

Preparation of a 1:1 molar mixture of 4-(tert-butyl)-2-((ethoxycarbonyl)oxy)phenyl benzoate and 5-(tert-butyl)-2-((ethoxycarbonyl)oxy)phenyl benzoate First Step:

30 g of 4-tert-butylcatechol (180 mmol) is charged in a round bottom flask with 90 mL of NaOH (2 mol/L) and 1.7 g of Na$_2$S$_2$O$_5$ (8.9 mmol). The mixture is cooled to 0° C. and 33.4 g of benzoyl chloride (220 mmol) in 40 mL of toluene are added dropwise slowly and the mixture is stirred for 4 hours. The reaction mixture is diluted with water and diethyl ether. The organic layer is separated and washed with 10% aqueous NaHCO$_3$, water, anhydrified over Na$_2$SO$_4$ and the solvent removed. The crude is distilled under vacuum to afford 19 g of a 1:1 mixture of 4-(tert-butyl)-2-hydroxyphenyl benzoate and 5-(tert-butyl)-2-hydroxyphenyl benzoate.

Second Step:

5.5 g of a 1:1 mixture of 4-(tert-butyl)-2-hydroxyphenyl benzoate and 5-(tert-butyl)-2-hydroxyphenyl benzoate (20.3 mmol) are charged in a flask with THF (30 mL), 2.4 g of pyridine (30.5 mmol) and 3.3 g of ethyl chloroformate (30.5 mmol). The reaction mixture is heated to 50° C. until GC shows that the reaction is completed. The mixture is quenched with aqueous HCl and diluted with diethyl ether. The organic layer is washed with water until neutral pH, then anhydrified over Na$_2$SO$_4$ and the solvent is distilled off to afford 9 g of crude which is distilled under vacuum to give 6 g of a 1:1 mixture of 4-(tert-butyl)-2-((ethoxycarbonyl)oxy)phenyl benzoate and 5-(tert-butyl)-2-((ethoxycarbonyl)oxy)phenyl benzoate.

Example 5

Preparation of a 1:1 molar mixture of 4-(tert-butyl)-2-((ethoxycarbonyl)oxy)-6-methylphenyl benzoate and 5-(tert-butyl)-2-((ethoxycarbonyl)oxy)-3-methylphenyl benzoate First Step:

10 g of 5-(tert-butyl)-3-methylcatechol (55.5 mmol) are charged under nitrogen in a round bottom flask with 110 mL of THF and 3.1 mL of triethyl amine (22.2 mmol). The mixture is cooled to 0° C. and 2.6 g of benzoyl chloride (18.5 mmol) are added dropwise. The reaction is kept at the same temperature until GC shows that benzoyl chloride is reacted completely. Then the mixture is quenched with aqueous HCl and diluted with diethyl ether. The organic layer is washed with water until neutral pH, then anhydrified over Na$_2$SO$_4$ and the solvent is distilled off. The crude obtained, which contains unreacted 5-(tert-butyl)-3-methylcatechol is subjected to stripping under high vacuum on heating to afford 2 g of a 1:1 mixture of pure 4-(tert-butyl)-2-hydroxy-6-methylphenyl benzoate and 5-(tert-butyl)-2-hydroxy-3-methylphenyl benzoate.

Second Step:

2 g of a 1:1 mixture of 4-(tert-butyl)-2-hydroxy-6-methylphenyl benzoate and 5-(tert-butyl)-2-hydroxy-3-methylphenyl benzoate (7 mmol) are charged in 10 mL of THF under nitrogen, in a round bottom flask and 0.2 g of NaH (7.8 mmol) are added portionwise. Then 1 mL of ethyl chloroformate (10.4 mmol) is added slowly and the mixture brought to reflux until GC shows that the reaction is completed. The mixture is quenched with aqueous HCl and diluted with diethyl ether. The organic layer is washed with water until neutral pH, then anhydrified over Na$_2$SO$_4$ and the solvent is distilled off to afford 2.3 g of a 1:1 mixture of pure 4-(tert-butyl)-2-((ethoxycarbonyl)oxy)-6-methylphenyl benzoate and 5-(tert-butyl)-2-((ethoxycarbonyl)oxy)-3-methylphenyl benzoate.

Comparative Example 1

Preparation of Diethyl pentane-2,4-diyl dicarbonate 5 g of 2,4-pentanediol (48 mmol) are charged in a round bottom flask, under nitrogen, with 70 mL of THF and 10.1 mL of ethyl chloroformate (0.106 mol). The mixture is cooled to 0° C. and 8.6 mL of pyridine (0.106 mol) in 10 mL of THF are added dropwise. The cooling bath is removed and the mixture is kept at room temperature for 2 hours. Then the mixture is quenched with aqueous HCl and diluted with diethyl ether. The organic layer is washed with water until neutral pH, then anhydrified over Na$_2$SO$_4$ and the solvent is distilled off to afford 10.7 g of pure diethyl pentane-2,4-diyl dicarbonate.

Synthetic Comparative Example 2

Preparation of pentane-2,4-diyl bis(3-chlorobenzoate)

The procedure is the same of Synthetic Comparative Example 1 except that 3-chlorobenzoyl chloride is used instead of ethyl chloroformate.

The so prepared donors are also listed in Table 1. The solid catalyst components prepared according to the general procedure were analyzed for their composition, and were tested in polymerization of propylene, using the method described above. The titanium and internal donor content of the solid catalyst components, and their performance in polymerization are also shown in Table 1.

TABLE 1

Composition and performance of exemplified catalysts

| Ex | Internal donor Name | % wt | Ti wt % | Mileage kg/g | XI wt % | MIL g/10' |
|---|---|---|---|---|---|---|
| 1 | 4-((ethoxycarbonyl)oxy)pentan-2-yl 4-propylbenzoate | 7.4 (97% syn, 3% anti) | 4.0 | 67 | 98.0 | 1.5 |
| 2 | 4-((ethoxycarbonyl)oxy)pentan-2-yl 3-chlorobenzoate | 14.0 (73% syn, 27% anti) | 5.3 | 60 | 96.1 | 3.1 |
| 3 | 4-((ethoxycarbonyl)oxy)butan-2-yl benzoate | 7.1 | 3.3 | 32 | 96.5 | 3.8 |
| 4 | 1:1 molar mixture of 4-(tert-butyl)-2-((ethoxycarbonyl)oxy)phenyl benzoate and 5-(tert-butyl)-2-((ethoxycarbonyl)oxy)phenyl benzoate. | N.D. | 3.7 | 64 | 97.5 | 1.1 |
| 5 | 1:1 molar mixture of 4-(tert-butyl)-2-((ethoxycarbonyl)oxy)-6-methylphenyl benzoate and 5-(tert-butyl)-2-((ethoxycarbonyl)oxy)-3-methylphenyl benzoate. | 17.2 | 3.9 | 54 | 98.4 | 1.2 |
| C1 | diethyl pentane-2,4-diyl dicarbonate | nd | 7.4 | 46 | 93.6 | 4.3 |
| C2 | pentane-2,4-diyl bis(3-chlorobenzoate) | 11.1 (96% syn, 4% anti) | 4.5 | 32 | 94.1 | 6.3 |

N.D. no data

What is claimed is:

1. A catalyst comprising:
a solid catalyst component for the polymerization of olefins comprising Mg, Ti and an electron donor compound of the following formula (I):

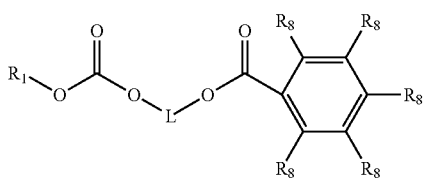

in which $R_1$ groups are selected from $C_1$-$C_{15}$ hydrocarbon groups, $R_8$ groups, equal or different to each other, are selected from hydrogen, halogen and $C_1$-$C_{15}$ hydrocarbon groups, optionally containing an heteroatom selected from halogen, O, P, S, N and Si and L is a divalent hydrocarbon group optionally containing heteroatoms selected from halogen, O, P, S, N and Si.

2. The catalyst according to claim 1 in which more than 50% of the total amount of donor has a syn configuration.

3. The catalyst of claim 1, comprising the product obtained by contacting:
a. the solid catalyst component,
b. triethylaluminum and, optionally,
c. an external donor compound.

4. The catalyst according to claim 1 in which $R_1$ groups are selected from $C_1$-$C_{10}$ alkyl groups and at least one of $R_8$ is different from hydrogen and selected from $C_1$-$C_{15}$ hydrocarbon groups or halogen.

5. The catalyst according to claim 4 in which $R_8$ is selected from $C_1$-$C_{10}$ alkyl groups or halogens.

6. The catalyst according to claim 4 in which the substituent $R_8$ different from hydrogen is located in meta or para position.

7. The catalyst according to claim 1 in which L is a divalent hydrocarbon group having a spacing chain between the two oxygen linked to it of from 2 to 6 carbon atoms and in which, independently, the said carbon atoms are optionally replaced by heteroatoms selected from halogen, O, P, S, N and Si and the hydrogen atom of the said divalent hydrocarbon group optionally, independently, are replaced by halogen or $C_1$-$C_{15}$ hydrocarbon groups, optionally containing an heteroatom selected from halogen, P, S, N and Si, which are optionally linked together or with the carbon atoms of said divalent group, to form saturated or unsaturated mono or polycyclic rings.

8. The catalyst according to claim 7 in which L is a divalent bridging group selected from $C_1$-$C_{20}$ alkylidene, $C_3$-$C_{20}$ cycloalkylidene, $C_6$-$C_{20}$ arylidene, $C_7$-$C_{20}$ alkylarylidene, or $C_7$-$C_{20}$ arylalkylidene radicals optionally containing heteroatoms selected from halogen, O, P, S, N and Si.

9. The catalyst according to claim 1 in which the donor belongs the following formula (II)

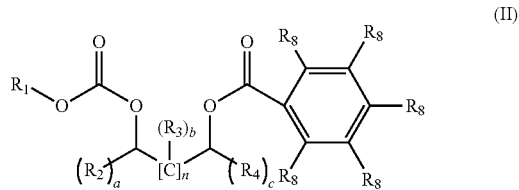

in which $R_2$ to $R_4$ groups, are equal to or different from each other, are hydrogen or $C_1$-$C_{15}$ hydrocarbon groups, optionally containing an heteroatom selected from halogen, P, S, N and Si; two or more of said groups are optionally linked together to form a saturated or unsaturated mono or polycyclic; n is an integer ranging from 0 to 3 and the indexes a, b, and c are, independently, 1 or 2.

10. The catalyst according to claim 9 in which when n is 0, both the indexes a and c are 2 and the groups $R_2$ and $R_4$ are, independently, selected from hydrogen and $C_1$-$C_{10}$ alkyl groups.

11. The catalyst according to claim 10 in which both $R_2$ and $R_4$ are methyl.

12. The catalyst according to claim 9 in which the donor has the following formula (IIa)

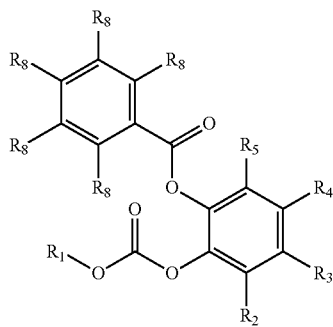

(IIa)

in which $R_2$-$R_5$ groups are selected from hydrogen or $C_1$-$C_{10}$ hydrocarbon groups.

13. The catalyst according to claim 12 in which two of $R_2$ to $R_5$ groups are hydrogen and the other two are selected from or C1-C10 linear or branched alkyl groups.

14. The catalyst according to claim 13 in which positions of the ring where substitution of hydrogen atoms takes place are positions 3 and 5.

15. The catalyst according claim 12 in which n is 1, the indexes a, b, and c are also 1 and the donor belongs to the following formula (III)

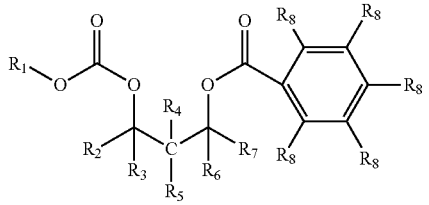

(III)

in which $R_2$ to $R_7$ groups, equal to or different from each other, are hydrogen or $C_1$-$C_{15}$ hydrocarbon groups, optionally containing an heteroatom selected from halogen, P, S, N and Si; two or more of said groups are optionally linked together to form a saturated or unsaturated cycle.

16. The catalyst according to claim 15 in which $R_4$ and $R_5$ independently, are hydrogen or $C_1$-$C_5$ alky groups.

17. The catalyst according to claim 15 in which the donor has the following formula (IV)

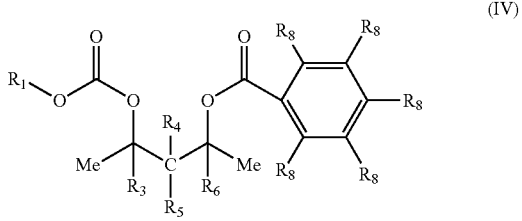

(IV)

in which $R_3$-$R_6$ groups are selected from hydrogen or $C_1$-CIO hydrocarbon groups.

18. The catalyst according to claim 17 in which $R_3$ to $R_6$ are hydrogen, $R_1$ is selected from $C_1$-$C_{10}$ alkyl groups and one of $R_8$ groups is different from hydrogen.

* * * * *

UNITED STATES PATENT AND TRADEMARK OFFICE
CERTIFICATE OF CORRECTION

PATENT NO.            : 9,487,599 B2                          Page 1 of 2
APPLICATION NO.       : 14/383838
DATED                 : November 8, 2016
INVENTOR(S)           : Alessandro Mignogna et al.

It is certified that error appears in the above-identified patent and that said Letters Patent is hereby corrected as shown below:

On the Title Page

| | | |
|---|---|---|
| Column 1, (30) | Line 1 | Delete "12158334" and insert --12158334.8-- |
| Column 2, (56) | Line 1 | Delete "Sesarch" and insert --Search-- |
| Column 2, (57) | Line 3 | After "formula (I)", insert --:-- |
| Column 2, (57) | Line 5 | Delete "In" and insert --in-- |

In the Specification

| | | |
|---|---|---|
| Column 1 | Line 2 | After "OLEFINS", insert --¶CROSS-REFERENCE TO RELATED APPLICATIONS-- |
| Column 1 | Line 7 | Delete "12158344.8" and insert --12158334.8-- |
| Column 2 | Line 42 | After "formula (I)", insert --:-- |
| Column 2 | Line 54 | Delete "¶In" and insert --in-- |
| Column 3 | Line 41 | After "below", insert --:-- |
| Column 4 | Line 16 | Delete "n" and insert --in-- |
| Column 4 | Line 22 | Delete "C1-C10" and insert --$C_1$-$C_{10}$-- |
| Column 4 | Line 49 | After "below", insert --:-- |
| Column 5 | Line 8 | After "below", insert --:-- |
| Column 5 | Line 21 | Delete "¶In" and insert --in-- |
| Column 10 | Line 47 | Delete "80 and 135° C." and insert --80 °C. and 135 °C.-- |
| Column 10 | Line 62 | Delete "80 to 120° C." and insert --80 °C. to 120 °C.-- |
| Column 11 | Line 7 | Delete "(100-130° C.)." and insert --(100 °C.-130 °C.).-- |
| Column 11 | Line 14 | Delete "(80-130° C.)" and insert --(80 °C.-130 °C.)-- |
| Column 11 | Line 19 | Delete "80-130° C." and insert --80 °C.-130 °C.-- |
| Column 11 | Line 60 | Delete "(II)" and insert --(ii)-- |
| Column 12 | Line 50 | Delete "20 to 120° C.," and insert --20 °C. to 120 °C.,-- |
| Column 12 | Line 50 | Delete "40 to 80° C." and insert --40 °C. to 80 °C.-- |
| Column 13 | Line 30 | After "Kg)", insert --.-- |
| Column 14 | Line 19 | After "reported", insert --.-- |

Signed and Sealed this
Twenty-second Day of January, 2019

Andrei Iancu
*Director of the United States Patent and Trademark Office*

CERTIFICATE OF CORRECTION (continued)
U.S. Pat. No. 9,487,599 B2

In the Claims

| | | |
|---|---|---|
| Column 18 | Line 51 | In Claim 9, after "formula (II)", insert --:-- |
| Column 19 | Line 11 | In Claim 12, after "formula (IIa)", insert --:-- |
| Column 19 | Line 33 | In Claim 13, delete "C1-C10" and insert --$C_1$-$C_{10}$-- |
| Column 19 | Line 39 | In Claim 15, after "formula (III)", insert --:-- |
| Column 20 | Line 21 | In Claim 17, after "formula (IV)", insert --:-- |
| Column 20 | Line 34 | In Claim 17, delete "C1-CIO" and insert --$C_1$-$C_{10}$-- |